United States Patent [19]

Turcotte

[11] 4,291,024

[45] Sep. 22, 1981

[54] CYTOTOXIC LIPONUCLEOTIDE ANALOGS

[76] Inventor: Joseph G. Turcotte, 30 Greenwood Dr, Peace Dale, R.I. 02879

[21] Appl. No.: 113,403

[22] Filed: Jan. 18, 1980

Related U.S. Application Data

[63] Continuation of Ser. No. 895,231, Apr. 10, 1978, abandoned.

[51] Int. Cl.³ .................. A61K 31/70; C07H 19/10; C07H 19/20
[52] U.S. Cl. ............................. 424/180; 536/27; 536/28; 536/29
[58] Field of Search ................ 424/180; 536/27–29

[56] References Cited

U.S. PATENT DOCUMENTS

| | | | |
|---|---|---|---|
| 3,787,392 | 1/1974 | Bergmeyer | 536/28 |
| 3,872,083 | 3/1975 | Okutsu et al. | 536/28 |

OTHER PUBLICATIONS

Srivastava, S., Diss. Abstr. Int. B 36, 4502, (1976).
Poorthuis, B., and Hostetler, K., Biochem. et Biophys. Acta, vol. 431, pp. 408–415, (1976).
Hostetler, K., et al., Biochem. et. Biophys. Acta, vol. 380, pp. 382–389, (1975).

*Primary Examiner*—Delbert R. Phillips
*Assistant Examiner*—Blondel Hazel
*Attorney, Agent, or Firm*—Haight, Rosfeld & Noble

[57] ABSTRACT

Nucleotides of nucleosides or bases having known cytotoxic activity are reacted to form corresponding cytotoxic liponucleotide analogs by phosphorylation of molecular species of phosphatidic acids. The resulting cytotoxic liponucleotide analogs exhibit an enhanced therapeutic index and broader spectrum of antitumor activity as compared to the parent nucleoside or base compounds, apparently due to an improved selective uptake thereof by metabolizing tumor cells, and are thus useful cytotoxic, antiviral and antineoplastic agents.

13 Claims, No Drawings

CYTOTOXIC LIPONUCLEOTIDE ANALOGS

This is a continuation of application Ser. No. 895,231 filed Apr. 10, 1978 now abandoned.

BACKGROUND OF THE INVENTION

This invention was funded in part by Grant Nos. CA 15898 and CA 13943 from the National Cancer Institute, National Institutes of Health.

This invention relates to a new class of cytotoxic liponucleotide analogs (sometimes abbreviated herein as CLNA) drugs having useful cytotoxic activity, to methods of preparing and using such drugs and to pharmaceutical compositions containing cytotoxically effective amounts of such drugs as a primary active ingredient.

Cancer can be considered as a group of diseases that can occur in any tissue, organ or system of the body. The causes of all cancers are not known, nor are there any reported major qualitative metabolic differences between cancer cells and host tissue cells of origin. Accordingly, cancer chemotherapy, unlike the chemotherapy of infectious diseases wherein the disease-causing organism itself offers a distinct metabolic or structural biologic target, has far more restrictive fundamental concepts on which to pattern therapeutic treatment.

Most known classes of anticancer drugs exert their action principally because of quantitative differences in metabolic rates of production or levels of certain nucleic acids, enzymes, proteins, hormones, metabolic intermediates, etc., rather than because of qualitative biologic differences between cancer cells and normal cells. Thus, anticancer drugs do not exhibit selective toxicity in the classical sense.

A number of anticancer nucleosides or bases have been described in the prior art. For example, cytosine arabinoside, 5-fluorouracil, 5-fluorodeoxyuracil, 6-mercaptopurine and thioguanine have become drugs currently used for the clinical treatment of cancer in human patients. In addition, preliminary clinical trials appear encouraging with respect to a dozen or more other drugs as have been reported by H. B. Wood, Jr. in "Drugs with Chemical Activity" and in "Some Unique Compounds in Development" published by the Drug Synthesis and Chemistry Branch, National Cancer Institute, January 1977, the contents of which are incorporated by reference herein. Literally scores of pyrimidines, purines, structurally related heterocyclic bases, nucleosides, etc., have been synthesized and demonstrated to possess high cytotoxic activity in cell culture and in a number of tumor-bearing animals; however, unfavorable therapeutic indexes have restricted the clinical use of this class of antimetabolites to relatively few antineoplastic drugs presently used for the chemotherapy of cancer.

OBJECTS OF THE INVENTION

Accordingly, it is a general object of the present invention to provide cytotoxic drugs which possess unique molecular structures and physicochemical properties because they are designed on the basis of the structure of naturally occurring liponucleotide metabolic molecules.

Another object of the present invention is to provide a new class of liponucleotide compounds which act as a new system for the delivery of cytotoxic agents to tumor cells.

A further object of the present invention is to provide a new class of cytotoxic drugs which, since they are phospholipid molecules themselves, can form lipid vesicles ("liposomes"), so that that penetrability of cancer cells can be achieved via the process of lysosomotropism or related membrane phenomena.

An additional object of the present invention is to provide anticancer nucleotides or higher phosphorylated forms of anticancer nucleosides which can be released within the cell via phospholipid-enzyme specific reactions or non-specific mechanisms, thus avoiding or circumventing dependency upon kinase activity or higher phosphorylation mechanisms which are essential for the manifestation of anticancer activity in most prior art clinically used anticancer nucleosides.

A more particular object of the present invention is to provide molecular species of cytotoxic liponucleotide analogs which are designed to interfere with the utilization or biosynthesis of cellular liponucleotides which are essential intermediates in the biosynthesis of phosphoglycerides and consequently essential for the biogenesis of cell membranes and for cell life.

Another important object of this invention is to provide cytotoxicly active compounds which exert quantitative and qualitative effects on humoral and cell-mediated immune mechanisms, including apparent immunostimulatory activity, and in which the cytotoxic and immunologic activities appear to be separable from each other, unlike similar drugs known in the prior art.

Upon study of the specification and appended claims, further objects, features and advantages of the present invention will become more fully apparent to those skilled in the art to which this invention pertains.

SUMMARY OF THE INVENTION

Briefly, the above and other objects, features and advantages of the present invention are attained in one aspect thereof by providing compounds of the general Formula 1, which shows the parent molecular structure of the cytotoxic liponucleotide analogs, or CLNA, according to the present invention, whose design is based on the molecular structure, biological function and properties of liponucleotides that occur in nature, e.g. cytidine diphosphate diglyceride and deoxycytidine diphosphate diglyceride.

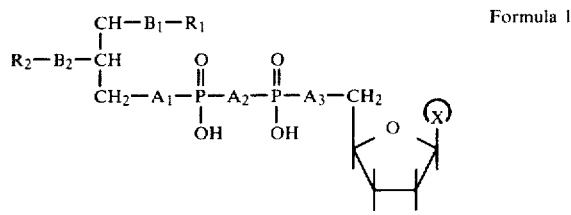

Formula 1 in which:

R$_1$ and R$_2$ are each predominantly straight, saturated or unsaturated fatty acid, alcohol, ester or amide chains of 6-24 carbon atoms each, preferably 12-20 carbon atoms and especially naturally occurring esterified fatty acids, e.g. obtainable from egg yolks, soybeans, etc.;

A$_1$, A$_2$ and A$_3$ are each independently divalent oxygen or methylene;

B$_1$ and B$_2$ are each independently divalent oxygen, methylene or the ester portion of a carboxylic acid ester;

heterocycle is a purine, primidine or hydrogenated pyrimidine, triazolopurine or similar nucleoside base; and sugar is a naturally occurring pentose or deoxypentose in the furanose form, preferably ribose, deoxyribose, lyxose, xylose or arabinose, provided that the sugar is not ribose or deoxyribose when the heterocycle is cytosine.

It can be seen from Formula 1 that a number of innovations can be made tailored onto the parent molecular structure, including:

(a) Utilization of any combination of single or multispecies fatty chains that vary in length and degree of unsaturation;

(b) "Replacement" of ester functions by ether, methylene, amide, etc. functions;

(c) Differences in configuration at the asymmetric lipid carbon, e.g. the R isomer, the S isomer or racemic (RS) mixtures;

(d) Variations in the phosphate ester portion, including options for mono-, di- and triphosphates and phosphonates, etc.

(e) Any number of variations in the sugar portions of the molecules, including deoxy forms and variations in stereochemistry of hydroxyl and base substituents; and (f) Variations in the nature of the heterocyclic bases, including any number of naturally occurring and/or "fraudulent" pyrimidine, purine or structurally related heterocyclic ring systems.

DETAILED DESCRIPTION

Liponucleotides (e.g. cytidine diphosphate diglyceride and deoxycytidine diphosphate diglyceride) have only recently (1975) been reported to occur in mammalian cells. Cytidine diphosphate diglyceride (CDP-diglyceride) is a vital intermediate in the biosynthesis of a number of classes of phosphoglycerides, including phosphatidyl inositol, phosphatidyl glycerophosphate, phosphatidyl glycerol and bis(phosphatidyl) glycerol (cardiolipin), and possibly phosphatidyl serine. UDP-diglyceride, GDP-diglyceride and ADP-diglyceride have also been found to be substrates for phosphoglyceride synthesizing enzymes, although they are less reactive than CDP-diglyceride. These liponucleotide substrates are unique in that they play an essential and highly specific role in the de novo biogenesis of phosphoglycerides, not only in animal tissue but throughout nature.

CDP-diglycerides (liponucleotides) are essential rate-limiting intermediates in the biosynthesis of plasma, mitochondrial, nuclear, etc. membrane phospholipids vital to cellular life. As they are furthermore present in extremely low concentrations and are rapidly turning over, they offer biochemically unique prototypes for the design of novel classes of antineoplastic agents. In addition, the physicochemical and metabolic properties of such molecules can be markedly altered by structural modifications in the nature of the hetereocycle, sugar, nucleoside (heterocycle + sugar), pyrophosphate function, carboxylic acid ester functions, fatty chains and stereochemistry as shown in Formula 1. It will be appreciated that the cytotoxic liponucleotide analogues (CLNA), as intact molecules, cannot properly be considered as merely derivatives or forms of existing anticancer nucleotides, but rather are true analogues of liponucleotides, a distinct class of naturally occurring molecules which have a vital natural metabolic role in the mammalian body.

Agents can be taken up selectively into cells and lysosomes via several mechanisms, e.g. by endocytosis, by permeation or by "piggyback" endocytosis; "piggyback" endocytosis is lysosomotropism conferred artificially on a substance by suitable formulation with an appropriate carrier and offers considerable potential in pharmacology and therapeutic drug development. A principal class of carriers of drugs requiring some such carrier for cell membrane transport, i.e., those drugs that do not enter cells naturally by endocytosis, are the phospholipid vesicles or liposomes that have received considerable attention recently. Examples of drugs that have been incorporated into liposomes for the purpose of studying the carrier potential of liposomes include cytosine arabinoside, 5'-fluorouracil, actinomycin D, methotrexate, bleomycin, colchicine, cyclic AMP, penicillin, local anesthetics, thyroid hormones and steroid hormones; other types of molecules (macromolecules) include proteins, enzymes, hormones (e.g. insulin), albumin, immunoglobulins, diphtheria toxoid and polynucleotides. All of these nucleoside drugs appear suitable for liponucleotide formation to form CLNA in accordance with the present invention.

Once the nucleotide is released from the CLNA molecule, the nucleotide is available for conversion into diphosphates, triphosphates, etc. and thereby can exert its cytotoxic effect via a number of possible mechanisms including effects on DNA polymerase, ribonucleoside diphosphate reductase, incorporation into DNA and inhibition of DNA and cellular metabolism in general.

Preferred compounds of the present invention are those of the above general Formula 1 meeting one or more of the following definitions:

(a) Compounds in which at least one, preferably two and especially all three of $A_1$, $A_2$ and $A_3$ are oxygen;

(b) Compounds in which $A_1$ is methylene while $A_2$ and $A_3$ are both oxygen;

(c) Compounds in which $A_2$ is methylene while $A_1$ and $A_3$ are both oxygen;

(d) Compounds in which $A_3$ is methylene while $A_1$ and $A_2$ are both oxygen;

(e) Compounds in which $B_1$ and $B_2$ are each ester groups, especially as in (a) thru (d) inclusive;

(f) Compounds in which $B_1$ is oxygen and $B_2$ is an ester group, especially as in (a) thru (d) inclusive;

(g) Compounds in which $B_1$ is methylene and $B_2$ is an ester group, especially as in (a) thru (d) inclusive;

(h) Compounds in which $R_1$ and $R_2$ are each multispecies mixtures, particularly of fatty acids and especially as in (a) thru (g) inclusive;

(i) Compounds in which $R_1$ is predominantly saturated, i.e. at least 90% saturated with some mononounsaturation, especially as in (a) thru (h) inclusive;

(j) Compounds in which $R_2$ is predominantly unsaturated, i.e. at least 90% monoethylenically or higher unsaturated, especially as in (a) thru (h) inclusive;

(k) Compounds in which the sugar is ribose, deoxyribose or arabinose, especially as in (a) thru (j) inclusive; and (l) Compounds in which the heterocycle is a purine, pyrimidine or analogue thereof, especially as in (a) thru (k) inclusive.

Compounds of this invention, in addition to those shown in the following Examples, include but are not limited to the following preferred compounds of the structure shown in Formula 1; more detailed examples of structural modifications of CLNA molecules are seen in Formula 2 and subgeneric Formula 3 as well as Lists 1 and 2; similar structural modifications can exist for mono- and tri-phosphate and/or phosphonate containing derivatives. $R_1$, $R_2$, $A_1$, $A_2$ and $A_3$ have the above-indicated values and Nu is a nucleoside base:

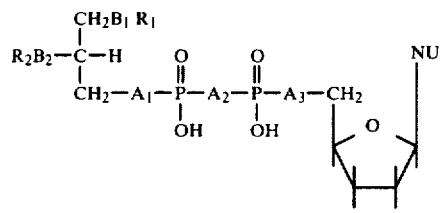

Formula 2

List 1

Detailed Examples of Possible Modifications of the Phosphorus Functions of Cytotoxic Liponucleotide Analogs (CLNA) of Formula 2; $R_1$ and $R_2$ are each derived from saturated, unsaturated or polyunsaturated fatty chains, while the sugar and heterocycle are as defined hereinabove.

|     | $A_1$ | $A_2$ | $A_3$ |
|-----|-------|-------|-------|
| Ia, | O | O | O |
| Ib, | O | O | $CH_2$ |
| Ic, | O | $CH_2$ | O |
| Id, | O | $CH_2$ | $CH_2$ |
| Ie, | $CH_2$ | O | O |
| If, | $CH_2$ | O | $CH_2$ |
| Ig, | $CH_2$ | $CH_2$ | O |
| Ih, | $CH_2$ | $CH_2$ | $CH_2$ |

List 2

Detailed Examples of Possible Modifications of the Phosphorus Functions of Cytotoxic Liponucleotide Analogs (CLNA) of Formula 3; $R_1$ and $R_2$ are each derived from saturated, unsaturated or polyunsaturated fatty chains, $A_1$, $A_2$, $A_3$ and Nu are as defined hereinabove.

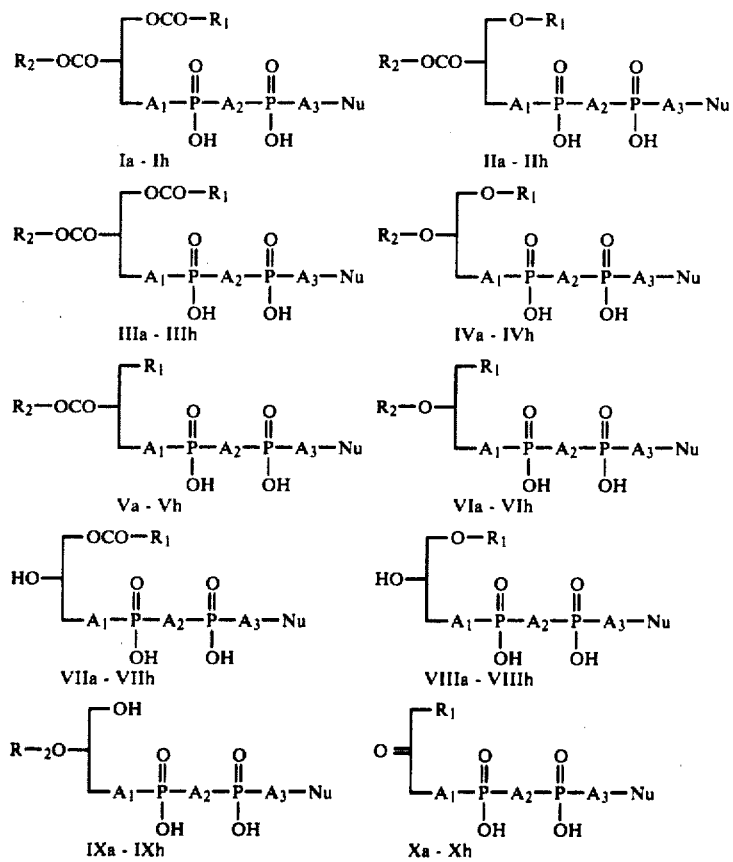

List 2. Some liponucleotide and lysoliponucleotide Analogs.
$R_1$ and $R_2$ = saturated, unsaturated, polyunsaturated fatty chain mixtures
Nu = sugar plus base (nucleoside).

List 1. Detailed Examples of Possible Structural Modifications of Glycerolipid and Phosphorus Moieties of Cytotoxic Liponucleotide Analogs (CLNA). R = Saturated, unsaturated, polyunsaturated fatty chains.

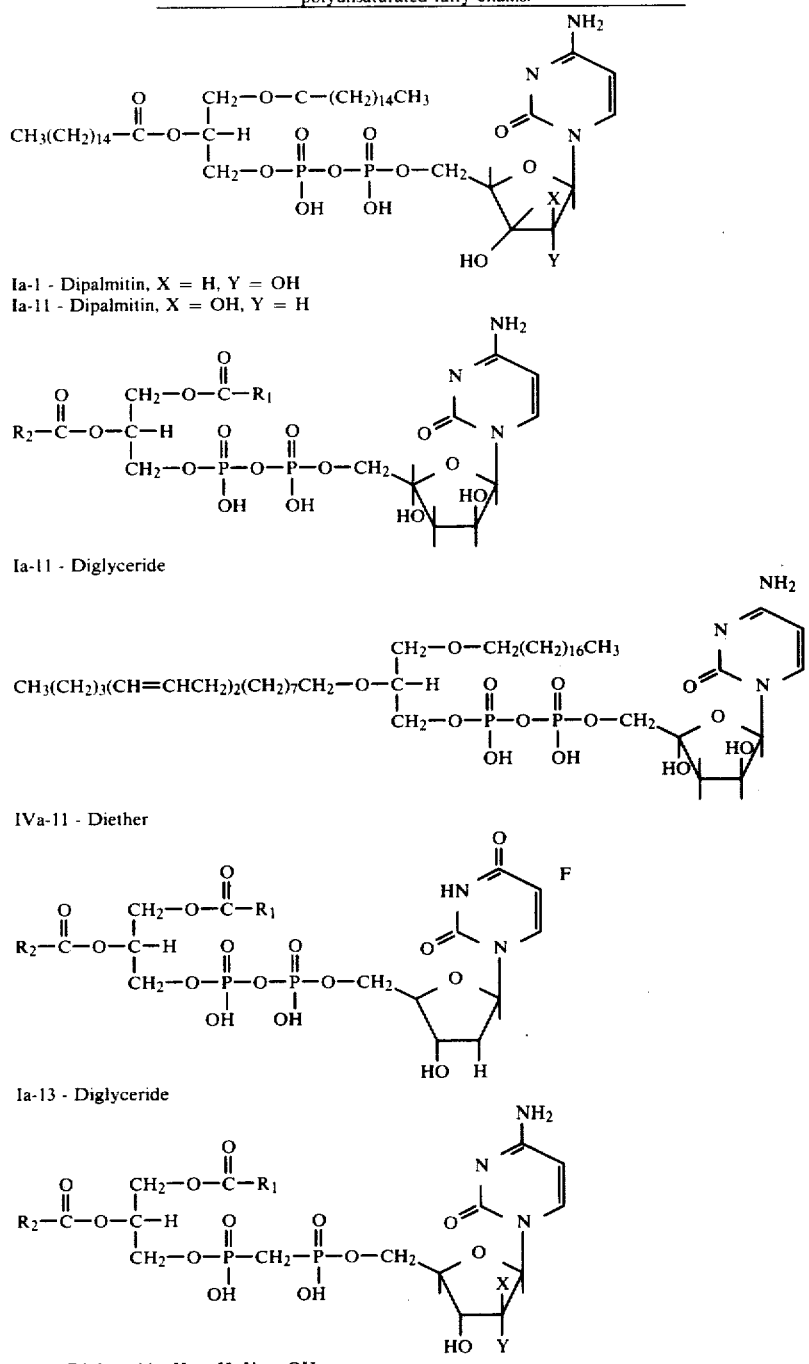

Ia-1 - Dipalmitin, X = H, Y = OH
Ia-11 - Dipalmitin, X = OH, Y = H

Ia-11 - Diglyceride

IVa-11 - Diether

Ia-13 - Diglyceride

Ic-1 - Diglyceride, X = H, Y = OH
Ic-11 - Diglyceride, X = OH, Y = H

List 2. Specific Examples of CLNA Molecules:
Ia-11-Dipalmitin; Ia-11-Diglyceride; IVa-11-Diether;
Ia-13-Diglyceride IC-1-Diglyceride and
Ic-11-Diglyceride Compounds of Formula I can be prepared from starting materials which themselves are known or can be prepared by methods analogous to those known in the art. The synthesis of liponucleotides of subclass Ia involves adaptations of reactions of multispecies phosphatidic acid with nucleotide morpholidates. Phosphatidic acids can be prepared in gram-quantities from readily available sources (egg yolk, soy bean flour, animal brain) of lecithin by treatment of the lecithin with phospholipase D or by total chemical synthesis. Liponucleotide synthesis can also utilize condensation of mono-protected phosphatidic acid and/or nucleoside phosphate esters, and possible advantages in yields via this approach compared with reaction of non-protected reactants remain to be determined. Nucleotides in general are prepared from corresponding nucleosides by direct phosphorylation using POCl$_3$ and trialkyl-phosphate(s); this method has been used to prepare the 5-phosphate of cytosine arabinoside and in good yield (60-70%, after purification) from the corresponding nucleoside. Conversion of nucleotides to morpholidates has been achieved in excellent yields (about 95%). A high-yield economic method for selective monophosphorylation of unprotected nucleosides at the 5'-hydroxyl functions recently has been developed through use of POCl$_3$-H$_2$O-pyridine in acetonitrile. Since the latter method as well as the POCl$_3$/trialkyl-phosphate method, have been found to be highly effective for the direct phosphorylation of a number of pyrimidine and purine nucleosides, these procedures would be the ones of choice, and would be anticipated to generally give high yields of the 5'-phosphates of selected nucleosides without use of protecting groups. However, syntheses utilizing protecting groups or other phosphorylating reagents might be employed for the preparation of nucleotide components of liponucleotides if a significant improvement in yield or other advantages would be warranted: e.g., pyrophosphoryl chloride/m-cresol or o-chlorophenol; di(2-t-butylphenyl)phosphorochloridate; cyanoethyl phosphate; 2,2,2-trichlorethylphosphorodichloridate; 2,2,2-trichloroethyl 2-chlorophenylphosphorochloridate; and dinitrobenzyl phosphorochloridate. The direct phosphorylation method is of sufficiently general utility to be an effective procedure to yield adequate quantitites of 5'-nucleotides, even if separation of other minor (2' and/or 3') isomers may be required in some instances; this would avoid longer synthetic approaches involving protective group chemistry. Chromatographic separation and purification of 5'-monophosphates and final product liponucleotides are then undertaken.

The synthesis of subclasses of liponucleotides which contain other than natural phosphatidic acid can be readily achieved by condensation of phosphatidic acid analogs, phosphotidic acids, or appropriate lipid derivatives with respective nucleosides, and/or phosphorylated or phosphonylated nucleosides. The chemical synthesis of the lipid derivatives can be undertaken using conventional synthesis starting with racemic or S-isopropylidine glycerol.

Some compounds of this invention which contain a center of asymmetry may be ordinarily obtained in the racemic form. The racemates can be separated into their optical antipodes in accordance with a plurality of known methods described in the literature; chemical separation is preferred. According to this procedure, diastereomers are formed from the racemic mixture by reaction with an optically active auxiliary agent. Thus, an optically active base can be reacted with the phosphate groups, or an optically active acid with the amino group, of a suitable compound of this invention. For example, diastereomeric salts of compounds containing a free phosphate group can be formed with optically active amines, e.g., quinine, cinchonidine, brucine, hydroxyhydrindiamine, morphine, 1-phenylethylamine, 1-naphthylethylamine, phenyloxynaphthylmethylamine, quinidine and strychnine or basic amino acids, e.g., lysine, arginine and amino acid esters; or diastereomeric salts of basic compounds can be formed with optically active acids, e.g., (+)- and (−)-tartaric acid, dibenzoyl-(+)- and -(−)-tartaric acid, diacetyl-(+)- and -(−)-tartaric acid, camphoric acid, beta-camphorsulfonic acid, (+)- and (−)-mandelic acid, (+)- and (−)-malic acid, (+)- and (−)-2-phenylbutyric acid, (+)- and (−)-dinitrodiphenic acid or (+)- and (−)-lactic acid. In a similar manner, ester distereomers can be produced by the esterification of compounds containing a free phosphate group with optically active alcohols, e.g., borneol, menthol or 2-octanol. The thus-obtained mixtures of diastereomeric salts and/or esters can be separated, e.g. by selective crystallization, and the desired optically active compounds can be produced by hydrolytic separation of the isolated diastereomeric compound.

A basic compound of the present invention can be converted into the associated acid addition salt with the use of an acid. For this reaction, suitable acids are those yielding physiologically acceptable salts. Suitable organic and inorganic acids are well known in the art and include but are not limited to aliphatic, alicyclic, araliphatic, aromatic and heterocyclic, mono- or polybasic carboxylic or sulfonic acids, e.g. formic acid, acetic acid, propionic acid, pivalic acid, diethylacetic acid, oxalic acid, malonic acid, succinic acid, pimelic acid, fumaric acid, maleic acid, lactic acid, tartaric acid, malic acid, aminocarboxylic acids, sulfamic acid, benzoic acid, salicyclic acid, phenylpropionic acid, citric acid, gluconic acid, ascorbic acid, nicotinic acid, isonicotinic acid, methanesulfonic acid, ethanedisulfonic acid, B-hydroxyethanesulfonic acid, p-toluenesulfonic acid, naphthalene mono- and -disulfonic acids, sulfuric acid, nitric acid, hydrohalic acids, e.g. hydrochloric acid and hydrobromic acid, and phosphoric acids, e.g. orthophosphoric acid.

Due to their cytotoxic, antineoplastic and immunopotentiating activity, the compounds of this invention are useful as antibacterial, antiviral and antineoplastic, especially antileukemic, agents in veterinary medicine. The compounds are effective against the same kinds of cell growth as their corresponding nucleoside or base parent compounds, wherein often exhibit an even broader range of activity against types of cancer not responsive to the parent compounds. In addition the their use in vitro, they can be employed, for example, in the oral, injection or perfusion therapy of cancers in substantially the same manner as the corresponding known parent nucleoside or base compounds, e.g. aracytidine.

The compounds of this invention can be employed in mixture with convention excipients, i.e. pharmaceutically acceptable organic or inorganic carrier substances suitable for parenteral, enteral or topical application which do not deleteriously react with the active compounds. Suitable pharmaceutically acceptable carriers include but are not limited to water, salt solutions, alcohols, vegetable oils, polyethylene glycols, gelatine, lactose, amylose, magnesium stearate talc, silicic acid, viscous paraffin, perfume oil, fatty acid monoglycerides and diglycerides, pentaerythritol fatty acid esters, hydroxy methylcellulose, polyvinyl pyrrolidone, etc. The pharmaceutical preparations can be sterilized and if desired mixed with auxiliary agents, e.g. lubricants, preservatives, stabilizers, wetting agents, emulsifiers, salts for influencing osmotic pressure, buffers, coloring, flavoring or aromatic substances and the like which do not deleteriously react with the active compounds.

For parenteral application, particularly suitable are solutions, preferably oily or aqueous solutions, as well as suspensions, emulsions or implants, including suppositories. Ampoules are convenient unit dosages.

For enteral application, particularly suitable are tablets, dragees, or capsules having a talc or carbohydrate carrier or binder or the like, the carrier preferably being lactose, corn starch or potato starch. A syrup, elixir or the like can be used wherein a sweetened vehicle is employed. Sustained release compositions can be formulated including those wherein the active compound is protected with differentially degradable coatings, e.g. by microencapsulation, multiple coatings, etc.

Generally, the compounds of this invention are dispensed in unit dosage form comprising 1–3,000 mg. of a pharmaceutical carrier per each unit dosage and the amount of active agent of the invention per unit dosage is about 1–200 mg.

For topical application, these are employed as vicous to semi-solid or solid non-sprayable forms comprising a carrier indigenous to topical application and having a dynamic viscosity preferably greater than water. Suitable formulations include but are not limited to solutions, suspensions, emulsions, cream, ointments, powders, liniments, salves, aerosols, etc. which are, if desired, sterilized or mixed with auxiliary agents, e.g., preservatives, stabilizers, wetting agents, buffers, salts for influencing osmotic pressure, etc. For topical application, also suitable are sprayable aerosol preparations wherein the active ingredient, preferably in combination with a solid or liquid inert carrier material, is packaged in a squeeze bottle or in admixture with a pressurized volatile, normally gaseous propellant, e.g., a freon. Usually, the active compounds of the invention are incorporated in topical formulations in a concentration of about 0.01 to 20 weight percent and are useful in the treatment of psoriasis and Herpes simplex infections.

The compounds of this invention are generally administered to animals, including but not limited to mammals and birds, e.g. humans. A cytotoxically effective daily dosage of the active compounds as administered intraperitoneally to mice generally comprises about 10 to 100, preferably about 50 mg/kg, together with 1–5,000 mg. of pharmaceutically acceptable carrier. The dose can be administered singly or as divided dosages throughout the day.

It will be appreciated that the actual preferred amounts of active compounds used will vary according to the specific compound being utilized, the particular compositions formulated, the mode of application, and the particular situs and organism being treated. Many factors that modify the action of the drug will be taken into account by those skilled in the art, e.g. age, body weight, sex, diet, time of administration, route of administration, rate of excretion, drug combinations, reaction sensitivities and severity of the condition being treated. Optimal application rates for a given set of conditions can be ascertained by those skilled in the art using conventional dosage determination tests in view of the above guidelines.

The compounds of the present invention are useful as intermediates in the production of other drugs, e.g. the parent nucleoside or nucleotide can be regenerated by hydrolysis of the phosphate ester bonds.

Preferred fatty acid derivatives for use in the compounds of the present invention are those single or mixtures, especially naturally occurring mixtures, of fatty acids having from six to 22 carbon atoms. The fatty acid chain is preferably straight chain but can be slightly branched, e.g. by substitution with few methyl or ethyl groups. Suitable fatty acids include but are not limited to hexanoic, octanoic, decanoic, lauric, myristic, palmitic, stearic and arachidic acids for the saturated fatty acids; oleic, linoleic, linolenic, arachidonic and similar unsaturated fatty acids. The unsaturated fatty acid derivatives can be in the cis-, trans- or both configurations and can contain alkylene-interrupted unsaturation or be conjugated diolefinically unsaturated as well as acetylenically unsaturated.

Monovalent heterocyclic ring substituents encompassed by the present invention are generally of 5–10, preferably 6–10 ring atoms of which 1–4, generally 1–3 and preferably 1 or 2, are oxygen, nitrogen and/or sulfur heteroatoms. The heterocyclic ring can be nonhydrogenated, e.g., imidazolyl, thiazolyl, etc.; partially hydrogenated, e.g., imidazolinyl, oxazolinyl, thiazolinyl, etc.; or completely hydrogenated, e.g., piperazinyl, morpholino, tetrahydropyrimidinyl, etc.

Suitable heterocyclic groups can be those derived from a five member heterocyclic ring containing a single heteroatom, e.g., furyl, thienyl or pyrrolyl; a five member heterocyclic ring containing two heteroatoms; e.g., pyrazolyl, imidazolyl, oxazolyl, oxazolinyl, isoxazolyl, isoxazolinyl, thiazolyl or thiazolinyl; a five member heterocyclic ring containing three heteroatoms, e.g., triazolyl, oxadiazolyl, thiadiazolyl, dioxazolyl and oxathiazolyl; or a five member heterocyclic ring containing four heteroatoms, e.g., tetrazolyl, oxatriazolyl and thiatriazolyl.

Suitable heterocyclic groups can be those derived from a six member heterocyclic ring containing a single heteroatom, e.g., pyridyl and pyranyl, preferably tetrahydropyridyl; a six member heterocyclic ring containing two ring heteroatoms, e.g., thiopyranyl, dioxinyl, pyridazinyl, pyrazinyl, piperazinyl, oxazinyl and morpholino, preferably pyrimidinyl, dihydropyrimidinyl and tetrahydropyrimidinyl; or a six member heterocyclic ring containing three ring heteroatoms, e.g., triazinyl, oxathiazinyl and oxadiazinyl, preferably triazinyl. Preferred heterocyclic groups derived from a six member heterocyclic ring are tetrahydropyridyl, pyrimidinyl, dihydropyrimidyl, tetrahydropyrimidyl and triazinyl.

Suitable heterocyclic groups can furthermore be those derived from a fused heterocyclic ring containing one or two six-membered rings fused to a five-membered ring wherein the six-membered ring is preferably interrupted by two nitrogen atoms and wherein the five-membered ring contains one or two, preferably two nitrogen or sulfur heteroatoms, e.g., purine and triazolopurine.

Preferred heterocyclic bases for the compounds of Formulae 1, 2 and 3 include but are not limited to cytosine, uracil, thymine, adenine, guanine, dihydrouracil, 5-fluorouracil, 5-azauracil, 6-azauracil, 5-azabytosine, 6-azacytosine, tetrahydropyridine dione, 2-amino tetrahydropyridine dione, 6-mercaptopurine, thioguanine, selenoguanine, 8-azaadenine-7-carboxamide, N-methyl-2-amino-1,2,4-triazolopurine and analogs.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever. In the following Examples, the temperatures are set forth uncorrected in degrees Celsius; unless otherwise indicated, all parts and percentages are by weight. The values obtained in elemental analyses are within commonly accepted limits of error.

EXAMPLE 1

1-Beta-D-Arabinofuranosylcytosine-5'-diphosphate-L-diglyceride Diammonium Salt

A mixture of 0.2 M acetate buffer (pH 5.6, 130 ml), 1.0 M aqueous $CaCl_2$ solution (36 ml), and phospholipase-D (150 mg) was stirred for 30 minutes at 25°. A suspension of 3.0 g of egg lecithin in 70 ml $Et_{2O}$ was added to the above mixture and stirred at 25° for 4 hr. The progress of the reaction was checked by TLC; when the reaction was completed (4–5 hr.), the ether was removed by a $N_2$ stream. The reaction product was extracted with 200 ml of $CHCl_3/CH_3OH$ (1:1, v:v). The chloroform phase was separated and then again extracted with 100 ml of $CHCl_3$. The chloroformic phases were combined, washed twice with 50 ml volumes of $H_2O$ and the solvent was removed under reduced pressure. The residue was dissolved in $Et_2O$ and the solution was dried over $Na_2SO_4$ and filtered. The filtrate was concentrated to a volume of about 40 ml and phosphatidic acid, mostly as the calcium salt, was precipitated by addition (ca 150 ml) of $CH_3OH$. The mixture was allowed to cool (ca 5°) overnight and centrifuged; the precipitate was washed with cold acetone and with 95% ethanol, then dried to yield 1.8 g of phophatidic acid, mostly as a calcium salt.

The phosphatidic acid (500 mg), chloroform (20 ml), methanol (20 ml), and 0.1 N HCl (20 ml) was mixed well in a separator. The chloroform phase was separated and evaporated to dryness with 10 ml of benzene. The residue was lyophilized and thoroughly dried under reduced pressure ($10^{-1}$ mm Hg). The dry phosphatidic acid, 470 mg (0.636 mmol), and 1-beta-D-arabinofuranosylcytosine 5'-(hydrogen morpholino phosphonate) compound with N,N'-dicyclohexyl-4-morpholine carboxamidine (1:1), 660 mg (0.802 mmol), was suspended in 20 ml of dry benzene and evaporated to dryness. The evaporation process (20 ml dry benzene) was repeated and 25 ml of dry distilled pyridine was added to the dry residue; the mixture then was stirred in a tightly stoppered flask at room temperature for four days. Pyridine was removed by a vacuum pump at 30° and the residue in the flask was dried in a vacuum desiccator over $H_2SO_4$ for 16 hr. The residue, almost free from pyridine, was shaken with 50 ml of chloroform-methanol (1:1, v:v) and 20 ml of 0.1 N ice-cold HCl. The chloroform phase was removed. The aqueous phase was once more extracted with 10 ml of $CHCl_3$. The chloroformic layers were combined and carefully washed with 10 ml of cold $H_2O$ to avoid excessive emulsion formation. The aqueous layer was removed and the chloroform phase was dried over $Na_2SO_4$ and filtered; the residual $Na_2SO_4$ and flask were washed with $CHCl_3$, followed by filtration. The filtrates were combined and concentrated under reduced pressure. The residue was deposited on a short, wide column (2.75×3.0) of silica gel. The column was eluted with chloroform and then with increasing concentrations of methanol in chloroform. Most of the unreacted phosphatidic acid was eluted with 20 to 25% methanol in chloroform; the product was eluted with $CHCl_3/MeOH$ (1:1, v:v) and had traces of impurities, mainly phosphatidic acid. Fractions containing the desired product (TLC) were combined and the pH of the eluate (pH=6.5) and was brought to 7.5 (pH meter) with methanolic $NH_4OH$. The solvent was evaporated and the residue was dissolved in 20 ml of chloroform/pyridine/formic acid 80% (50:30:7, v:v:v) and applied to a second silica column (2×25 cm) prepared in the same solvent system and eluted with 200 ml of the same mixture. The column was eluted with $CHCl_3/MeOH$ (9:1, v:v), the methanol concentration being gradually increased to 50% to elute the desired product. The desired fractions were combined and the solvent evaporated to ca 2–3 ml to obtain a white precipitate. To this mixture cold acetone (5 ml) was added and the suspension was centrifuged. The supernatant was discarded and the residue was dissolved in a mixture of 10 ml of chloroform methanol (2:1, v:v); cold 0.1 N HCl was added to pH 2.5. The aqueous phase was discarded and washed with $H_2O$ by centrifugation. The chloroform phase was brought to pH 7.5 with 2 N methanolic ammonium hydroxide and the solvent was evaporated under reduced pressure. The residue was thoroughly dried in a vacuum desiccator over $P_2O_5$ to give 300 mg of a white amorphous solid: mp yellow, then brown ca 180°, melts (brown mass) 218°–220° C. dec; $R_f$(TLC) 0.72 [silica, $CHCl_3/MeOH/H_2O$/glacial HOAc (25:15:4:2)]; ir (KBr) 2915, 2849, 1724, 1575 (broad), 1235 (broad), 1117, 1064 (broad), 926 (broad), 784 (broad), 712 (broad).

EXAMPLE 2

1-Beta-D-Arabinofuranosylcytosine-5'-diphosphate-DL-1,2-dipalmitin Diammonium Salt 2, 3-Dihexadecylglycerylphosphoric acid (103 mg, 159 umol) and 1-beta-D-arabinofuranosylcytosine 5'-(hydrogen morpholino phosphonate) compound with N,N'-dicyclohexyl-4-morpholine carboxamidine (1:1) (153 mg, 223 umol) were suspended in 10 ml of benzene and the mixture was evaporated; the evaporation process then was repeated two more times. Pyridine (15 ml) was added rapidly to the reaction mixture, which then was stirred (magnetic bar) for 70 hours at room temperature (25°) in a tightly stoppered ground glass flask. Most of the solvent was removed under reduced pressure (10–15 mm/oil pump) and the product in the original reaction flask was dried in vacuo (0.5–1.0 mm) over concentrated $H_2SO_4$ in a desiccator for one day. The product, a light-yellow-colored solid film, was dissolved in 10 ml of ice-cold water, and 0.5 N HCl was added dropwise to the solution until the pH was 2.0; the mixture appeared as a white flaky solid suspended in $H_2O$. To the acidified suspension was added 15 ml of $CHCl_3$-MeOH (1:1) and the mixture was shaken gently. An emulsion readily formed which was broken upon letting the mixture stand in the cold (ice-bath) for ca one-half hour. The chloroform layer was separated and the aqueous phase was extracted two more times with 15-ml portions of $CHCl_3/MeOH$ (1:1). To the separated and then combined chloroform phases 10 ml of $MeOH/H_2O$ (2:1) was added and pH of the solution was brought to 7.8 with 2 N methanolic $NH_4OH$. The aqueous phase was separated and the chloroform phase was repeatedly (4–5 times) extracted with $MeOH/H_2O$ (2:1). The original aqueous phase and the combined $MeOH/H_2O$ extracts then were placed in a beaker and the solution was concentrated to about 1 ml with a stream of $N_2$. To the concentrated mixture 10 ml of acetone was added which resulted in further deposition of a white solid. The mixture then was kept at −40° for 2–3 hours, centrifuged and the solvent removed by decantation. The white amorphous solid was washed with 2 ml of Et$_2$O and was dried in vacuo (0.5–1.0 mm) over P$_2$O$_5$ for two days at room temperature to give 50 mg (30% yield) of an amorphorous off-white-colored solid: mp 170° (softened), 190° dec; R$_f$(TLC) 0.68 [silica, CHCl$_3$/MeOH/H$_2$O/glacial HOAc (25:15:4:2)], 0.67 [n-propanol/conc NH$_4$OH/H$_2$O (20:20:3)]; ir (KBr) 3226, 2915, 2849, 1724, 1460, 1227, 1111, 1058, 943, 800 and 717; 1H NMR (pyridine-d$_5$) 1.00 (distorted t, CH$_3$), 1.40 (s, CH$_2$), 2.25–3.05 (poorly resolved m, CH$_2$CO), 4.20–4.90 (broad unresolved m centered at 4.50, CH$_2$O, CHO, CHN), 5.10–6.09 (unresolved m), 7.30–7.75 (unresolved m); uv$_{max}$[MeOH/H$_2$O(2:1)] 276 nm.

| Analysis: (C$_{44}$H$_{87}$N$_5$O$_{15}$P$_2$) | | | | |
|---|---|---|---|---|
| | C | H | N | P |
| Theoretical: | 53.47 | 8.87 | 7.08 | 6.28 |
| Found: | 53.70 | 8.99 | 6.81 | 6.10 |

In subsequent experiments, 35–40% yields were obtained.

EXAMPLE 3

1-Beta-D-Arabinofuranosylcytosine-5'-diphosphate-DL-Di-O-(2-octadecadienyl-3-octadecyl)-1-glycerophosphate diammonium salt 2-(9,12-Octadecadienyloxy)-3-(octadecyloxy)-1-propanol dihydrogen phosphate (100 mg) was dried by evaporation from benzene two times, mixed with 120 mg of 1-beta-D-arabinofuranosylcytosine 5'-(hydrogen morpholino phosphonate) compound with N,N'-dicyclohexyl-4-morpholine carboxamidine (1:1) and evaporated with 10 ml of benzene. Dry pyridine (15 ml) was added and the mixture was stirred at 30° for six days in a stoppered flask. Pyridine then was removed under reduced pressure and the residue dried in a vacuum desiccator over H$_2$SO$_4$ for 24 hr. to remove the last traces of pyridine. The residue in the flask was dissolved in 20 ml of CHCl$_3$/CH$_3$OH (1:1) and to the solution was added 10 ml of ice-cold 0.1 N HCl. The lower chloroform phase was separated and the upper aqueous phase was extracted again with 10 ml of CHCl$_3$. The combined CHCl$_3$ phase was washed with 10 ml H$_2$O, dried over Na$_2$SO$_4$, and filtered. The filtrate was evaporated under reduced pressure to give 104 mg of a residue, which was dissolved in a minimal volume of CHCl$_3$. The solution was deposited on a column (2.5×10 cm) of silica (SilicAR CC-7) and eluted with chloroform followed by gradually increasing concentrations of MeOH. Fractions containing the desired product were pooled and neutralized to pH 8.0 with methanolic ammonium hydroxide. The solvent was removed under reduced pressure and the residue dried in a vacuum desiccator to yield 25 mg of a white amorphous solid: R$_f$ 0.72 [silica, CHCl$_3$/CH$_3$OH/H$_2$O/glacial HOAc (15:15:4:2)]. The entire sample was used for antitumor evaluation.

EXAMPLE 4

1-Beta-D-Arabinofuranosylcytosine-5'-diphosphate-DL-O-(2,3-dihexadecyl)-1-glycerophosphate diammonium salt A solution of 220 mg (0.35 mmol) of 2,3-dihexadecylglycerylphosphoric acid in benzene (ca 10 ml) was swirled in a reaction flask while cooling in a dry ice-acetone bath to coat the walls with an "even" layer; 1-beta-D-arabinofuranosylcytosine 5'-(hydrogen morpholino phosphonate) compound with N,N'-dicyclohexyl-4-morpholine carboxamidine (1:1) (240 mg, 0.35 mmol) was similarly suspended in benzene and distributed on the walls of the flask. The mixture was lyopholized for 48 hours and then pyridine (20 ml) was added; the fluffy white solids dissolved almost immediately. The mixture then was allowed to stand at room temperature for 72 hours. The solvents were removed under reduced pressure (vacuum pump, lukewarm water bath) and the last traces of pyridine were removed by placing the reaction vessel in a vacuum desiccator over concentrated sulfuric acid. The resultant material (yellow-color solid film) was dissolved in H$_2$O (40 ml) and cooled, and the pH was adjusted to 2.0 with 0.5 NHCl which caused formation of a flaky white precipitate suspended in the water. The suspension was shaken with 30 ml of a CHCl$_3$/MeOH (1:1) solution to give an emulsion which separated after standing in an ice bath for 0.5 hours; the aqueous layer was extracted twice more in this fashion. The combined chloroform layers were stored overnight at −80° C. After evaporation of the solvents under reduced pressure, the residue (ca 400 mg) was dissolved in chloroform/pyridine/formic acid (50:30:7) and applied to a silica gel column (30 g) packed with the same solvent. The column was eluted consecutively with the chloroform/pyridine/formic acid (50:30:7) (150 ml), chloroform (500 ml), and methanol/chloroform mixtures (200 ml each of 5%, 10%, 15%, 20%, 25% and 37%, respectively) finally the product was eluted using 50% MeOH/CHCl$_3$. Upon evaporation of the solvents under reduced pressure, two very minor spots corresponding to diphosphate diglyceride byproducts were noted. The pH of the material was adjusted to 7.8 with 2 N NH$_4$OH (methanolic) and the material stored overnight at −80°. The product was an unknown mixture of salts produced by catonic exchange from the silica gel packing. Conversion of the salt to the acid form was effected by titration with 0.5 N HCl acid to pH 2.0. The free acid was extracted with CHCl$_3$/MEOH (1:1) solution (3×30 ml) and after the addition of ca 10 ml H$_2$O, the pH was adjusted to 8.0 with 2 N NH$_4$OH (methanolic). The solvents were evaporated under reduced pressure and the residue transferred to a tared centrifuge tube by washing with CHCl$_3$/MEOH (1:1) solution. The solvents were evaporated under a stream of nitrogen to about 3 ml and the product precipitated by the addition of about 10 ml acetone with stirring. Centrifugation and decantion of the solvent, was followed by drying the predcipitate in the centrifuge tube in a vacuum desiccator for 24 hours to give 80 mg (23.7%) of an off-white solid: R$_f$(TLC) 0.78 (silica) CHCl$_3$:MeOH":H$_2$O:HOAc (25:15:4:2); ir (KBr) 3393, 2923, 2857, 1724, 1645, 1466, 1230, 1129, 1053, 943, 794, 718.

| Analysis: (C$_{44}$H$_{91}$N$_5$O$_{13}$P$_2$) | | | |
|---|---|---|---|
| | C | H | P |
| Theoretical: | 55.04 | 9.55 | 6.45 |
| Found | 55.07 | 9.54 | 6.19. |

EXAMPLE 5

1-Beta-D-Ribofuranosylcytosine-5'-Diphosphate-DL-1,2-Dipalmitin Diammonium Salt (Control)

The salt (0.300 g, 491 umol) was suspended in 20 ml of dry C$_6$H$_6$ and phosphatidic acid 2,3-dihexadecylglycerylphosphoric acid (0.339 g, 440 umol), dissolved in 15 ml of dry $C_6H_6$, was quantitatively transferred to the flask containing the diphosphate diglyceride reactant. The mixture was solidified by placing the flask in a dry ice-acetone bath and rotating, and then lyophilized (0.5–1.0 mm) to constant weight. Anhydrous pyridine then was added and the flask was immediately closed tightly (standard joint glass stopper) and the reaction mixture was allowed to stir for 65 hr. at room temperature. The solvent was removed under reduced pressure (30°) and the original flask was left in a desiccator over concentrated sulfuric acid under vacuum (0.5–1.0 mm) overnight. The residue, 0.598 g, was dissolved in 15 ml of ice-cold water-the pH of the solution was 8.0. Hydrochloric acid (0.5 N), then was added dropwise to the solution until the pH was 2.9 (precipitation). To the suspension 15 ml of MeOH and 15 ml of $CHCl_3$ was added and the mixture was shaken well (emulsion) in a separatory funnel. The emulsion was allowed to break (0.5–1 hr), the $CHCl_3$ phase separated, and the aqueous phase was extracted twice with 10-ml portions of $CHCl_3$. To the combined chloroform phase 15 ml of $MeOH/H_2O$ (2:1) was added and the pH was brought to 8.2 with 2 N methanolic $NH_4OH$. The mixture was shaken and centrifuged, the upper aqueous phase was withdrawn and the chloroform phase was extracted two more times with 15-ml portions of a $MeOH/H_2O$ (2:1) solution. The combined aqueous-methanolic extract was filtered and concentrated with a stream of nitrogen blown on the surface of the liquid in a beaker. After the volume was reduced to 1–2 ml, 25 ml of cold acetone was added and the mixture (covered) was left in a freezer at $-40°$ for 2–3 hours. A white amorphous solid was separated by centrifugation which then was washed with 2 ml of $Et_2O$. The resultant product was dried under high vacuum (0.5–1.0 mm) at room temperature to give 163.4 mg (37.5% yield) of a slightly grey-colored solid: mp 170° (softened), 190° dec; $R_f$ (TLC) 0.68 [silica, $CHCl_3/MeOH/H_2O$/glacial HOAc (25:15:4:2)] [n-propanol conc $NH_4OH/H_2O$ (20:20:3)]; ir (KBr) 3226, 2915, 2849, 1724, 1460, 1227, 1111, 1058, 943, 800, 717; $uv_{max}$ [$MeOH/H_2O$(2:1)] 276 nm.

| Analysis: ($C_{44}H_{82}N_5O_{15}P_2$) | | | | |
|---|---|---|---|---|
| | C | H | N | P |
| Theoretical | 53.47 | 8.87 | 7.08 | 6.28 |
| Found | 53.42 | 8.85 | 6.80 | 6.28 |

ANTITUMOR AND IMMUNOLOGIC DATA

Results of antitumor evaluations thus far carried out are presented in Tables 1–6. Antitumor testing was done by Drs. Ming Y. Chu and Lance M. Tibbetts, Division of Biological and Medical Sciences, Brown University and Roger Williams General Hospital, Providence, Rhode Island.

a. Against reproduction of murine leukemic cell L5178Y growth in culture (Tables 1 and 2) cytotoxic liponucleotide analogs (CLNA) were found to be less active than the 5'-phosphate ester of cytosine arabinoside, a clinically used anticancer drug; however, against the same leukemic cell growth in vivo, CLNA derivatives Ia-11-diglyceride. (Table 4) and Ia-11-dipalmitin (Table 5) both were found to be significantly more active than cytosine arabinoside. These results support the concept that the "whole" liponucleotide analog molecule is responsible, at least in part, for enhanced antineoplastic activity.

b. That the "whole" liponucleotide molecule has a role in elaboration of antitumor activity is also suggested by the leukemic cell kill in culture (Tables 1 and 2) and in the peritoneal cavity (Table 3) caused by liponucleotide Ia-1-dipalmitin, a ribose-containing representative molecular species of naturally occurring liponucleotide; Ia-1-dipalmitin does not contain a "cytotoxic" (i.e., anticancer) moiety, yet appeared to have activity comparable to the CLNA molecule containing the beta-D-arabinofuranosyl moiety in two test systems (see Tables 1 and 3).

c. Differences in antitumor activity in culture among cytotoxic liponucleotide molecules exist due to variations in the lipid composition of the molecules, as indicated by the superior activity of Ia-11-diglyceride as compared with Ia-11-dipalmitin (Table 2).

d. The in vivo activity of the cytotoxic liponucleotide analog Ia-11-diglyceride as compared with cytosine arabinoside in mice bearing leukemia L5178Y cells (Table 4) is highly significant and encouraging. The prolongation of survival times (93%) achieved with 50 mg/kg/day$\times$4 of Ia-11-diglyceride represents a 4-log cell kill in contrast to an essentially insignificant prolongation (18%) obtained with cytosine arabinoside using the same dose and dose regimen. Both Ia-11-diglyceride ($LD_{10}=85$ mg/kg/day$\times$4) and cytosine arabinoside ($LD_{10}=71$ mg/kg/day$\times$4) were administered at does regimens below their respective $LD_{10}$ values. The difference in in vivo antitumor activity between Ia-11-diglyceride and cytosine arabinoside is more striking and apparent when one considers the molecular weights of each of the molecules. On this basis 50 mg of Ia-11-diglyceride is "equivalent" to about 13 mg of cytosine arabinoside, so that the 93% change in life span (Table 4) obtained with Ia-11-diglyceride was at a dose "equivalent" to about 13 mg/kg of the latter molecule; put another way, administration of doses of 13 mg/kg$\times$4 of cytosine arabinoside to animals bearing this tumor would result in no change in life spans as compared with control animals.

e. A significant difference in antitumor activity in vivo exists between the multispecies CLNA derivative Ia-11-diglyceride (Table 4) and the single molecular species Ia-11-dipalmitin (Table 5). This finding suggests important differences in lipid vesicle formation and/or properties, which in turn may contribute to observed differences in cancer cell kill.

f. With human colon carcinoma HCT-15 cells grown in mice immunosuppressed with antithymocyte serum, Ia-11-diglyceride at 50 mg/kg/day$\times$4 significantly inhibited the tumor growth (excised tumors weighed) by 80% of the control non-treated control animals (Table 6); in contrast, cytosine arabinoside at 200 mg/kg/day$\times$4 showed no inhibition of tumor cell growth as determined by palpation. Although toxicity (Table 6) was observed with Ia-11-diglyceride in this animal model, the activity observed against implanted colon carcinoma growth is extraordinary, since cytosine arabinoside is not effective against solid tumors in general.

g. Ia-11-Diglyceride exhibited a more pronounced suppression of IgM and IgG mouse antisheep erythrocyte antibody-forming cells (AFC) than could be predicted from its cytosine arabinoside "equivalent." Immunological testing was done by Dr. Jeffrey A. Levy, Roger Williams General Hospital, Providence, R.I.

Ia-11-Diglyceride given intraperitoneally at 50 mg/kg/day×4 reduced both IgM and IgG AFC/$10^6$ spleen cells and AFC/spleen to background levels. In contrast, cytosine arabinoside at 11 mg/kg/day×4 only reduced the peak (day 4) number of IgM AFC/$10^6$ spleen cells from 495±130 to 180±28 (63% reduction) and peak (day 5) number of IgG AFC/$10^6$ spleen cells from 494±123 to 224±72 (55% reduction). At 50 mg/kg/day×4, cytosine arabinoside reduced AFC to background levels. Neither temporal delays nor IgG enhancement were seen at any drug level tested. CMI-DTH reactions were poorly suppressed by cytosine arabinoside at 11 or 50 mg/kg. Ia-11-Diglyceride, however, at 50 mg/kg delayed peak response 3 days (day 4-7) or more, and may have immunostimulatory activity on DTH at later periods as judged by the very late rising profile of response.

untreated controls; inhibition by ara-CDP-dipalmitin at $1.0 \times 10^{-4}$ M was less than 50%.

TABLE 3

ANIMAL ANTITUMOR ACTIVITY OF LIPONUCLEOTIDES

| | | PERCENT SURVIVAL | | |
|---|---|---|---|---|
| LIPONUCLEOTIDE | CONTROL | 20 mg/kg | 40 mg/kg | 100 mg/kg |
| Ia-1-Dipalmitin | 100 | 57 | 54 | 43 |
| Ia-11-Dipalmitin | 100 | 61 | 58 | 43 |

The leukemic cells L5178Y ($4 \times 10^5$ cells/mouse) were injected intraperitoneally on day 0. Drugs at various dosages (20 mg/kg, 40 mg/kg and 100 mg/kg) were injected on day 5 and incubated for 2 hours. At the end of the incubations, 5.0 ml of Fischer's medium contain-

TABLE 1

INHIBITION OF REPRODUCTION OF MURINE LEUKEMIC CELLS L5178Y BY LIPONUCLEOTIDES - 2 HOURS

| | | PERCENT SURVIVAL | | | |
|---|---|---|---|---|---|
| MOLECULE | CONTROL | $1 \times 10^{-7}$M; | $1 \times 10^{-6}$M; | $1 \times 10^{-5}$M; | $1 \times 10^{-4}$M |
| Ia-11-Dipalmitin | 100 | 94.7 ± 5.03; | 94.7 ± 4.04; | 76.7 ± 6.66; | 65.7 ± 5.69 |
| Ia-11-Dipalmitin | 100 | 94.0 ± 3.00; | 90.0 ± 4.58; | 84.3 ± 0.58; | 65.0 ± 1.73 |
| Cytosine Arabinoside 5'-Phosphate | 100 | 99.0 ± 5.21; | 93.0 ± 8.90; | 87.5 ± 5.18; | 54.8 ± 1.54 |

L5178Y cells ($2 \times 10^5$/ml) in the exponential phase of growth were incubated singly with drugs for a period of 2 hours at concentrations of $1 \times 4^{-4}$ M to $1 \times 10^{-7}$ M. Cell viability was determined by the dilute agar colony method. Each observation represents the mean value of three experimentations with four replicates per experiment. A minimum of 200 colonies were counted for each group. The cloning efficiency of the untreated cells was approximately 75%; all values were normalized to 100%.

TABLE 2

INHIBITION OF REPRODUCTION OF MURINE LEUKEMIC CELLS L5178Y BY CYTOTOXIC LIPONUCLEOTIDE ANALOGS - 72 HOURS

| MOLECULE | MOLAR CONCENTRATION CAUSING 50 PERCENT INHIBITION | PERCENT INHIBITION AT $10^{-4}$M |
|---|---|---|
| Ia-11-Diglyceride | $3.5 \times 10^{-6}$ | |
| Ia-11-Dipalmitin | $1.4 \times 10^{-5}$ | |
| Ia-1-Diaplmitin | | 42 |
| IVa-11-Diether | $1.5 \times 10^{-5}$ | |
| Cytosine Arabinoside 5'-Phosphate | $2.7 \times 10^{-7}$ | |

The leukemic cells L5178Y were grown from an inoculum of $4 \times 10^3$ cells per ml for a period of 72 hours in the presence of different levels ($10^{-4}$–$10^{-7}$ M) of drugs. The final number of cells were determined with a Coulter Particle Counter, Model 2BI and the 50% inhibitions were determined as the amounts of drugs required to cause a 50% decrease in the number of doublings of the cell population undergone when compared with the ing 10% horse serum (FMS) was injected sterily (I.P.). After mixing, 1.0 ml aliquots were withdrawn and transferred to culture tubes containing 5.0 ml of FMS. Cells were centrifuged immediately, washed 2 xs and resuspended in 5.0 ml of FMS. Cell viability was determined by the dilute agar colony method.

TABLE 4

EFFECT OF CYTOTOXIC LIPONUCLEOTIDE ANALOG Ia-11-DIGLYCERIDE ON THE SURVIVAL TIME OF MICE BEARING LEUKEMIA L5178Y ASCITES CELLS

| MOLECULE | DAILY DOSAGE (mg/kg) | AVERAGE SURVIVAL (DAYS ± S.E.) | % CHANGE IN LIFE SPAN | % CHANGE IN WEIGHT |
|---|---|---|---|---|
| CONTROL | 0 | 17.6 ± 0.2 | 0 | +0.66 |
| Ia-11-Diglyceride | 12.5 | 22.0 ± 0.6 | +29.6 | +2.02 |
| | 25.0 | 25.4 ± 1.1 | +44.3 | +1.56 |
| | 50.0 | 34.0 ± 2.4 | +93.2 | -0.30 |
| Cytosine Arabinoside | 50.0 | 20.7 ± 5.4 | +17.6 | -6.90 |

Mice (10/group) were inoculated with L5178Y cells ($5 \times 10^6$ cells/mouse) and drug injections were begun on the second day. The drug in a volume of 0.1 ml was injected intraperitoneally once a day for four consecutive days. Saline was administered to the controls. The percent change in body weight from the onset to the termination of therapy was used as an indication of drug toxicity.

TABLE 5

EFFECT OF CYTOTOXIC LIPONUCLEOTIDE ANALOG Ia-11-DIPALMITIN ON THE SURVIVAL TIME OF MICE BEARING LEUKEMIA L5178Y ASCITE CELLS

| DAILY DOSAGE (mg/kg) | AVERAGE SURVIVAL (Days) | PER CENT CHANGE IN LIFE SPAN | PER CENT CHANGE IN WEIGHT |
|---|---|---|---|
| 0 | 15.0 ± 0.28 | 0 | -1.4 |
| 30 | 18.6 ± 0.22 | +24.0 | -5.0 |

TABLE 5-continued
EFFECT OF CYTOTOXIC LIPONUCLEOTIDE ANALOG Ia-11-DIPALMITIN ON THE SURVIVAL TIME OF MICE BEARING LEUKEMIA L5178Y ASCITE CELLS

| DAILY DOSAGE (mg/kg) | AVERAGE SURVIVAL (Days) | PER CENT CHANGE IN LIFE SPAN | PER CENT CHANGE IN WEIGHT |
|---|---|---|---|
| 30 | 19.8 ± 0.82 | +32.0 | −5.86 |
| 50 | 20.6 ± 0.76 | +37.3 | −3.5 |

Mice (10/group) were inoculated with L5178Y cells ($5 \times 10^6$ cells/mouse) and drug injections were begun on the second day. The drug in a volume of 0.2 ml was injected intraperitoneally twice a day at a five-hour interval for four consecutive days. Distilled water was administered to the controls. The percent change in body weight from the onset to the termination of therapy was used as an indication of drug toxicity.

TABLE 6
ANTITUMOR ACTIVITY OF CYTOTOXIC LIPONUCLEOTIDE ANALOG Ia-11-DIGLYCERIDE AGAINST HUMAN COLON CARCINOMA IN IMMUNOSUPPRESSED MICE

| DAILY DOSAGE (mg/kg) | TUMOR WEIGHT (mg) | PER CENT OF CONTROL TUMOR WEIGHT | PER CENT CHANGE IN BODY WEIGHT |
|---|---|---|---|
| 0 | 89.7 ± 4.9 | 0 | +18 |
| 25 | 61.3 ± 14.0 | 68.4 ± 15.6 | −11 |
| 50 | 18.7 ± 12.0 | 21.0 ± 13.5* | −20 |

*P 0.005 (1-tailed "t" test)

Male B6D2F1 mice (18–22 g, 4/group) were immunosuppressed with 0.25 ml subcutaneous injection of ATS on days −1,0,1,3 and 6. Human colon carcinoma cells ($5.0 \times 10^6$ cells/mouse) were inoculated subcutaneously into an area slightly above the left inguinal region on day 0. The drug dissolved in saline to a volume of 0.1 ml was injected intraperitoneally once a day for four consecutive days. Saline was administered to the controls. The percent change in body weight from the onset to the day of weighing the tumor was used as an indication of drug toxicity.

The preceding examples can be repeated with similar success by substituting the generically or specifically described reactants and/or operating conditions of this invention for those specifically used in the examples. From the foregoing description, one skilled in the art to which this invention pertains can easily ascertain the essential characteristics thereof and, without departing from the spirit and scope of the present invention, can make various changes and modifications to adapt it to various usages and conditions.

What is claimed is:

1. A compound selected from the group consisting of compounds of the formula:

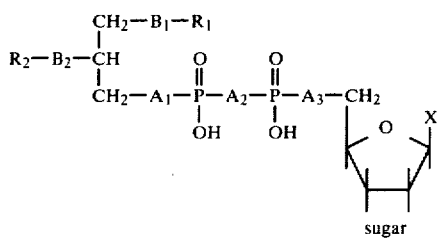

in which:

$R_1$ and $R_2$ are each predominantly straight, saturated or unsaturated multispecies fatty chains of 6–24 carbon atoms each;

at least one of $A_1$, $A_2$ and $A_3$ is methylene and the others of $A_1$, $A_2$ and $A_3$ are each independently divalent oxygen or methylene;

$B_1$ and $B_2$ are each independently divalent oxygen (—O—), methylene (—CH$_2$—), ester

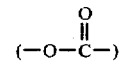

or amide

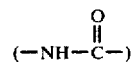

functions;

X is a nucleoside base selected from the group consisting of cytosine, uracil, thymine, adenine, guanine, dihydrouracil, 5-fluorouracil, 5-azauracil, 6-azauracil, 5-azacytosine, 6-azacytosine, tetrahydropyridine dione, 2-amino tetrahydropyridine dione, 6-mercaptopurine, thioguanine, selenoguanine, 8-azaadenine-7-carboxamide and N-methyl-2-amino-1,2,4-triazolopurine;

sugar is selected from the group consisting of ribose, deoxyribose, lyxose, xylose and arabinose, provided that the sugar is not ribose or deoxyribose when the heterocycle is cytosine;

and their physiologically acceptable acid addition salts.

2. A compound according to claim 1, wherein at least one of $A_1$, $A_2$ and $A_3$ is oxygen.

3. A compound according to claim 1, wherein $A_1$ is methylene while $A_2$ and $A_3$ are both oxygen.

4. A compound according to claim 1, wherein $A_2$ is methylene while $A_1$ and $A_3$ are both oxygen.

5. A compound according to claim 1, wherein $B_1$ and $B_2$ are each ester groups.

6. A compound according to claim 1, wherein $R_1$ is predominately saturated and $R_2$ is predominately unsaturated.

7. A pharmaceutical composition comprising a safe and cytotoxically effective amount of a compound according to claim 1 in combination with a pharmaceutically acceptable carrier.

8. A compound selected from the group consisting of compounds of the formula:

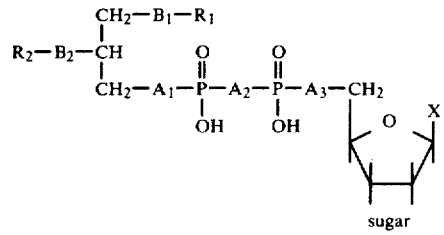

in which:

$R_1$ and $R_2$ are each predominantly straight, saturated or unsaturated multispecies fatty chains of 6–24 carbon atoms each, provided that $R_1$ does not equal $R_2$ when $R_1$ is $CH_3(CH_2)_{14}CO$—;

$A_1$, $A_2$ and $A_3$ are each independently divalent oxygen or methylene;

$B_1$ and $B_2$ are each independently divalent oxygen (—O—), methylene (—CH$_2$—), ester

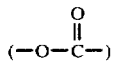

or amide

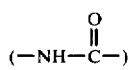

functions;

X is a nucleoside base selected from the group consisting of cytosine, uracil, thymine, adenine, guanine, dihydrouracil, 5-fluorouracil, 5-azauracil, 6-azauracil, 5-azacytosine, 6-azacytosine, tetrahydropyridine dione, 2-aminotetrahydropyridine dione, 6-mercaptopurine, thioguanine, selenoguanine, 8-azaadenine-7-carboxamide and N-methyl-2-amino-1,2,4-triazolopurine;

sugar is selected from the group consisting of ribose, deoxyribose, lyxose, xylose and arabinose, provided that the sugar is not ribose or deoxyribose when the heterocycle is cytosine, uracil, adenine or guanine;

and their physiologically acceptable acid addition salts.

9. A compound according to claim 8, wherein at least one of $A_1$, $A_2$ and $A_3$ is oxygen.

10. A compound according to claim 8, wherein $A_2$ is methylene while $A_1$ and $A_3$ are both oxygen.

11. A compound according to claim 8, wherein $B_1$ and $B_2$ are each ester groups.

12. A compound according to claim 8, wherein $R_1$ is predominately saturated and $R_2$ is predominately unsaturated.

13. A pharmaceutical composition comprising a safe and cytotoxically effective amount of a compound according to claim 8 in combination with a pharmaceutically acceptable carrier.

* * * * *